United States Patent [19]

Brackenridge

[11] 4,079,035

[45] Mar. 14, 1978

[54] HALOPHENOXYPHOSPHAZENE FIRE RETARDANTS AND POLYESTERS CONTAINING SAME

[75] Inventor: David R. Brackenridge, Royal Oak, Mich.

[73] Assignee: Ethyl Corporation, Richmond, Va.

[21] Appl. No.: 661,864

[22] Filed: Feb. 27, 1976

Related U.S. Application Data

[63] Continuation-in-part of Ser. No. 525,871, Nov. 21, 1974, abandoned, which is a continuation-in-part of Ser. No. 392,978, Aug. 30, 1973, abandoned, which is a continuation-in-part of Ser. No. 205,383, Dec. 6, 1971, abandoned.

[51] Int. Cl.$^2$ .................. C08L 67/04; C08L 67/06
[52] U.S. Cl. .................. 260/45.9 NP; 260/2.5 AJ; 260/15; 260/40 R; 260/45.9 R; 260/75 N; 260/864
[58] Field of Search ............ 260/45.9 R, 2.5 AJ, 260/40 R, 864, 47 P, 45.9 NP, 75 N; 106/15 FP

[56] References Cited

U.S. PATENT DOCUMENTS

| | | | |
|---|---|---|---|
| 2,109,491 | 3/1938 | Lipkin | 252/49.9 |
| 2,192,921 | 3/1940 | Lipkin | 260/461 |
| 3,206,494 | 9/1965 | Lund | 260/461 |

FOREIGN PATENT DOCUMENTS

| | | |
|---|---|---|
| 924,731 | 4/1973 | Canada. |
| 2,062,677 | 11/1971 | Germany. |

*Primary Examiner*—Lester L. Lee
*Attorney, Agent, or Firm*—Donald L. Johnson; John F. Sieberth; Robert A. Linn

[57] ABSTRACT

The fire retardancy of polyesters is enhanced with halophenoxyphosphazenes which are reaction products of a halogenated phenol and a phosphonitrilic halide. Brominated phenols are preferred although chlorophenols can be used. Of the brominated phenols, preferred starting materials are p-bromophenol, 2,4-dibromophenol and mixtures thereof. Phosphonitrilic chlorides are preferred starting materials. Pure phosphonitrilic halides can be used; however, mixtures are preferred because of their availability. Cyclic and linear phosphonitrilic halides are useful as well as mixtures thereof. Saturated and unsaturated polyesters can be made fire retardant by this invention as can thermoplastic and thermosetting materials. Linear and crosslinked polyesters can be treated. Preferred polyesters are fiber forming polyesters of a diol and dibasic acid, such as poly(ethylene terephthalate) and poly(1,4-cyclohexylenedimethyleneterephthalate).

19 Claims, No Drawings

HALOPHENOXYPHOSPHAZENE FIRE RETARDANTS AND POLYESTERS CONTAINING SAME

CROSS REFERENCE TO RELATED APPLICATION

This is a continuation-in-part of copending aplication Ser. No. 525,871, filed Nov. 21, 1974, which in turn is a continuation-in-part of application Ser. No. 392,978, filed Aug. 30, 1973, which in turn is a continuation-in-part of application Ser. No. 205,385, filed Dec. 6, 1971; all said prior applications now being abandoned.

BACKGROUND OF THE INVENTION

Phosphazenes and their preparation are disclosed in U.S. Pat. No. 2,109,491. Partially substitued materials are mentioned in U.S. Pat. No. 3,206,494. p-Bromophenoxyphosphazenes are known, Dell et al, *J. Chem. Soc.* 4070 (1965). High molecular weight poly(phenoxyphosphazene) has been described; Kugel et al *Inorganic Chem.* 5, 1709 (1966).

Phosphonitrilic halides can be prepared by reacting $NH_4Cl$ with $PCL_5$; Emsley et al, *J. Chem. Soc.* (A), 768 (1971). Other references dealing with this preparation are cited therein and mentioned below.

Various fire retardants have been suggested for polyesters; confer for example, U.S. Pat. Nos. 2,909,501, 3,285,995, 3,309,425, 3,434,981, 3,794,617, and Canadian Pat. No. 924,731. Hexaphenoxyphosphazene had been suggested for fire retarding polyester fibers.

SUMMARY OF THE INVENTION

This invention provides novel halogen-substituted aryl phosphazenes. It also provides a polyester compositions containing a fire retardanct amount of a halophosphazene.

In a preferred embodiment, I provide phosphazenes that are reaction products of a phosphonitrilic chloride and a halophenol selected from mono-, di-, and trihalophenols, such phosphazenes having at least 10

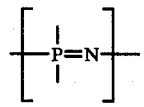

units, and a molecular weight of from about 3900 to about $2 \times 10^7$. Of these phosphazenes I prefer those having a melting point about 200° 1 C., more preferably those melting from about 200° C. to about 300° C., and especially those melting between about 280°-300° C. Preferred halophenols are p-bromophenol, 2,4-dibromophenol, and mixtures thereof.

In particular embodiments of this invention, I provide phosphazenes made from p-bromophenol which are a. essentially linear and have a molecular weight of from about 10,000 to about 34,000, b. essentially linear and have a molecular weight of about $10^7$; and c. essentially cyclic, have little or no cyclic trimer, and as a major portion contain cyclic tetramer, cyclic pentamer, or mixture thereof, and with a molecular weight from about 1900 to about 6600.

In another embodiment, I provide as a composition of matter, polyester stabilized with a fire retardant amount of a phosphonitrilic halide and a halogenated monohydroxyaromatic compound.

The polyester may be saturated or unsaturated. I prefer saturated, fiber-forming polyester condensation products of a diol and a dicarboxylic acid, or ester of such acid, selected from isophthalic acid, terephthalic acid and saturated aliphatic dibasic acids having 2 to about 10 carbon atoms.

The halogenated monohydroxy aromatic compounds used to make the phosphazenes may contain substituents other than hydroxy and halogen, and their exact nature is not critical. Preferably, they have an isolated benzene nucleus of up to about 12, more preferably up to about 10 carbon atoms. I prefer that the phosphazene be derived from a halogenated phenol, preferably a brominated phenol such as the monobromo-, dibromo-, and tribromophenol. Of these, I prefer p-bromophenol, 2,4-dibromophenol, and mixtures thereof.

In one embodiment, I provide a composition of matter comprising (a) a fiber-forming polyester of a diol and a dicarboxylic acid selected from the class consisting of isophthalic acid, terephthalic acid and saturated aliphatic dibasic acids of 2 to about 10 carbon atoms, and (b) a fire retardant amount of a phosphazene having the formula

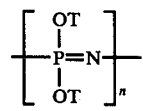

where n is 3 or more and T is a monohydroxy aromatic radical having the formula

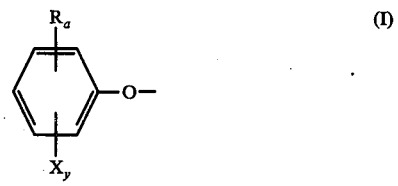

wherein R is an alkyl group of up to about 3 carbon atoms, a is an integer of from 0–4 such that the number of carbon atoms in said aromatic compound does not exceed about 10, X is selected from chlorine and bromine, and y is an integer of from 1–5.

In another embodiment, I provide polyester stabilized with a flame retardant amount of condensation product of phosphonitrilic dihalide and a brominated phenol having the formula

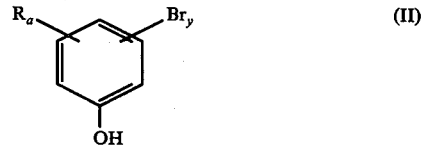

wherein R is an alkyl radical of up to about 3 carbon atoms, a is an integer of value 0–3 such that the total number of carbon atoms in radicals appended to the ring is not more than about 4 and y is an integer of value 1–5; said polyester being selected from the class consisting of saturated polyester fiber made from ethylene glycol and an acid selected from the class consisting of isophthalic and terephthalic acid, and unsaturated polyester resin made from said alcohol and a mixture of maleic acid and another acid selected from the class consisting of isophthalic and terephthalic acid, said mixture being crosslinked with a material selected from the class consisting of divinylbenzene and styrene.

For fiber-forming polyester, I prefer to use phosphazene fire retardants having a melting point above about 200° C. More preferably, the melting point is from about 200° to about 300° C., most preferably about 280°-300° C.

In particular embodiments of this invention, I provide polyester fibers with a fire retardant amount of one of the following phosphazenes derived from $(PHCl_2)_n$ and p-bromophenol:

a. an essentially linear composition having a molecular weight of from about 10,000 to about 34,000, b. an essentially linear composition having a molecular weight of about $10^7$, and c. an essentially trimer-free, essentially cyclic composition having as a major portion a fraction selected from cyclic tetramer, cyclic pentamer, and mixtures thereof, and having a molecular weight of from about 1900 to about 6600. A preferred fire retardant concentration in the polyester substrate is about 5-30 weight percent.

The novel phosphazenes of this invention can be used as fire retardants for polyester as indicated above. Fire retardant polyester of this invention has a variety of uses. For example, the unsaturated polyesters can be used as structural materials on board ships and boats. Polyester fibers flame retarded according to this invention can be used to make protective clothing. The polyester fiber can be used along or blended with other fibers such as cotton or wool. Films can be made from solutions or suspensions of the phosphazene fire retardants of high molecular weight provided herein. The materials having a molecular weight of about $10^7$ can be made into fire retardant film and fibers. The fibers can be woven into fabric which also contains polyesters.

DESCRIPTION OF PREFERRED EMBODIMENTS

As indicated above, a major aspect of this invention comprises use of phosphazenes as fire retardants for polyester.

Polyesters include linear and crosslinked polymers. The linear materials are prepared by reacting dibasic acids with glycols and are thermoplastic in nature. Typically, the glycol is ethylene glycol and the acid is isophthalic or terephthalic acid. Fibers can be spun from such materials and films can be made therefrom.

A larger group of polyesters is the unsaturated resins. These are used for reinforced shapes and coatings. For these resins, unsaturated acids or alcohols are incorporated in the polymer. By "unsaturated" is meant the presence of an active carbon-to-carbon double bond. Through this unsaturated bond, crosslinking is achieved. For example, if some of the phthalic acid in the polymer above is replaced by maleic acid, then crosslinking can be achieved using divinylbenzene or styrene. To achieve this crosslinking, a curing agent is mixed with the polymerizable mixture; typically, the curing agent is an organic peroxide.

Unsaturated polyesters of this type are called alkyd resins in the paint industry. They have many advantageous properties such as strength, weather resistance, pigmentability, etc.

As is well known, unsaturated polyester resins are based on prepolymers which are made by the esterification of dihydric alcohols with unsaturated and modifying dibasic acids and/or anhydrides. The unsaturated polymer is mixed with an unsaturated monomer, (e.g. styrene) with which it crosslinks. A catalyst, polymerization inhibitor and inert filler are among the typical additives; *Chemical Economics Handbook*, 580.1230E, Plastics and Resins, Stanford Research Institute (1969).

Polyester fibers are made by direct esterification, for example, reaction of terephthalic acid with ethylene glycol, or by transesterification. In the latter route, there is a catalyzed exchange of ethylene glycol for methyl groups, say of dimethyl terephthalate. The liberated methanol is removed by distillation to drive the exchange to completion. The 2-hydroxyethylenephthalate so-formed undergoes polycondensation, usually in the presence of a catalyst, to form the polymer. This may be broken into chips, blended, and remelted before spinning. Alternatively, the polymer can be made and continuously fed to spinnarets. *Chemical Economics Handbook, Fibers-Synthetic,* 543.4820G December, 1969, Stanford Research Institute, Menlo Park, California.

Polyester resins of the above types are well known in the prior art; confer for example, U.S. Pat. No. 2,909,501, 3,285,995, 3,309,425, 3,434,981; and *Unsaturated Polyesters,* Boenig, Elsevier Publishing Co., New York, N.Y. (1964). Descriptions of such resins in these works are incorporated by reference herein as if fully set forth. Some unsaturated resins which are articles of commerce, for example, the Glaskyd and Laminac Resins made available by American Cyanamid Company.

In a preferred embodiment, the polyesters are fiber-forming polymers and fibers and fabrics by the reaction of glycols of the general formula

$$HO-(CH_2)_x-OH$$

wherein $x$ is an integer from about 2 to about 10 with a dibasic acid. Such glycols include ethylene glycol, which is a preferred glycol, 1,3-propanediol, 1,5-pentanediol, 1,6-hexanediol, 1,7-heptanediol, 1,8-octanediol, 1,4-nonanediol, 1,10-decanediol or the like. These glycols, and particularly the preferred glycols ethylene glycol and 1,4-cyclohexanedimethanol, are reacted with dicarboxylic acids or suitable esters thereof, preferably terephthalic acid or dimethyl terephthalate, or other dibasic acids including isophthalic acid, adipic acid, sebacic acid, succinic acid, oxalic acid, glutaric acid, pimelic acid, suberic acid, azelaic acid and the like. In addition to being useful with polyesters derived from the more common diols and dicarboxylic acids the diol may be used as a reactive intermediate with other reactants including glycerol, sorbitol, pentaerythritol, methoxypolyethylene, glycol, neopentyl glycol, monohydroxypivalate, trimethylolpropane, trimesic acid, p,p'-dicarboxydiphenoxyethane, p-carboxyphenoxyacetic acid, and the like.

In the more preferred embodiment the polyester fibers are derivatives of terephthalic acid such as poly(ethyleneterephthalate) or poly(1,4-cyclohexylenedimethyleneterephthalate).

Small amounts of other monomers may also be incorporated to alter one or more of the properties of the polyester. For example, small amounts of butanediol or isophthalic acid may be incorporated therein. Also, to improve the disperse dyeability of the polyester, small amounts of dibasic acids such as adipic acid, azelaic acid or dimer acids may be used. Sulfonated isophthalic acid may be employed to improve the basic dyeing properties of the polyester. In general, however, the amounts of these reactants should not exceed about 3 mol percent of the polyester. Rather than modifying the polyester in this manner it may be more advantageous to enhance the desired properties thereof by blending the polyester with an amount of a suitable additive including other polyester or copolyester compositions. Polyester and copolyester fibers which may be treated effectively in accordance with the present invention include those described in U.S. Pat. No. 2,465,319 and 2,901,466. Such fiber-forming polyesters as described above have inert viscosities usually greater than about 0.4.

Especially for use with polyester fibers, I prefer those phosphazenes of a halogenated phenol which have a melting point of above about 200° and about 300° C. A highly preferred melting point range is from about 280° to about 300° C.

Materials with the above melting characteristics, in general, can be readily admixed with molten polyester. Of course, one can use materials melting at other temperatures, if desired, especially if they are soluble in the polyester substrate at a temperature within about 200° to about 300° C.

Preferably, the fire retardant will not unduly decompose or volatilize at processing temperatures. In this regard, it is preferred that weight loss on heating be not substantially greater than the weight loss of the polyester substrate. In general, weight loss on heating should be about the same as the polyester substrate, although phosphazenes having a slightly greater weight loss can be used.

For fibers, color stability of the fire retardant is an important consideration. It is preferred that the fire retardant undergo little or no discoloration when heated under an inert gas at processing temperature for processing times. Thus, the fire retardant should not undergo discoloration to a desirable degree at 200°–300° C., while under nitrogen.

Fire retardant phosphazenes for this invention preferably contain less than about 50 ppm $H_2O$ by weight and HBr and HCl concentrations should be less than 0.1 weight percent.

The fire retardant should have some permanency in the fiber. In other words, the fire retardant phosphazene should be retained in the fabric to provide fire retardancy after laundering or dry cleaning. The degree of permanency desired will depend on the application of the fiber or fabric as will be recognized by a skilled practitioner. Thus, to pass a Children's Sleep Wear Test (DOC FF 3-71) flammability protection must exist after 50 washings. Other applications do not require this high degree of permanency. For example, some drapery material applications require retention of the fire retardant for five or less dry cleanings.

Furthermore, the fire retardant should not render the fiber tacky. To avoid an undesirable degree of tackiness, the fiber must retain the fire retardant so that the fire retardant does not migrate to an undesirable extent to the polymeric fiber surface. To avoid an undesirable amount of this migration and to provide a desirable quantum of permanency in the fiber, I use a phosphazene having 10 or more

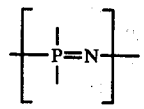

monomeric units. Preferably the number of such units is high enough to provide a molecular weight of at least about 3900 and preferably at least 10,000 as set forth more fully below.

Halogenated phosphazene-polyester compositions provided herein have an unexpected amount of ultraviolet stability.

In accordance with this invention, a fire retardant amount of condensation product of phosphonitrilic halide and a brominated phenol is admixed with a polyester of the type described above. The mixing can be accomplished by a technique known to a skilled practitioner. Thus, for example, the flame retardant agent can be thoroughly mixed with molten polymer before feeding to the spinnaret. In instances when it is desirable to lessen or minimize the time of exposure to high temperatures, it may be desirable to admix the fire retardant with the polyester very near (and downstream from) the spinnaret. Furthermore, the agent can be milled or molded with the resin, or blended with a prepolymer-unsaturated monomer mixture. In general, from about 2 to about 40 weight percent or more additive is used. More preferably, from about 5 to about 30 weight precent additive is employed and most preferably from about 10 to about 20 weight percent.

As pointed out above, this invention comprises use of phosphazenes as flame retardants and the phosphazenes are derived from halogenated monohydroxy aromatic compounds. The exact nature or structure of the hydroxy aromatic compound is not critical and many of them are applicable in this invention. Of the applicable halogenated hydroxy aromatic compounds certain are preferred. First of all, it is preferred that they be derivatives of bromine or chlorine. In other words, it is preferred that the halogenated hydroxy aromatics be a chloro compound or a bromo compound.

Secondly, it is preferred that the halogenated monohydroxy aromatic compound react without an untoward amount of difficulty with the phosphonitrilic halide. For this reason, it is preferred that the hydroxy aromatic be not too bulky so as to inhibit the reaction by steric hindrance. Likewise, it is preferred that groups adjacent to the hydroxy group should not interfere to an undesirable amount with the ability of the hydroxy group to react with a halogen atom in the phosphonitrilic halide.

With regard to the size of the hydroxy aromatic compound it is preferred that it possess an isolated benzene nucleus. By this I mean preferred hydroxy aromatics are derivatives of benzene rather than naphthalene or some other fused ring system. An isolated benzene nucleus, for purposes of this invention, is a benzene ring which is not involved in a fused ring system. More preferably, the applicable halogenated aromatics with the isolated benzene nucleus are also devoid of substituents which hinder reaction to an undesirable extent. For this reason, and for their greater availability, I prefer to use halogenated hydroxy aromatic compounds wherein the isolated benzene nucleus has up to 12, and more preferably up to 10, carbon atoms.

Furthermore, it is preferred that any substituents on the isolated benzene nucleus be comparatively small so as to avoid steric problems referred to above. For this reason, I prefer substituents to be lower alkyl such as alkyl groups of up to three carbon atoms. If such substituents are ortho to the hydroxy group, I prefer the groups to be primary rather than secondary or tertiary.

Another reason for preferring simple rather than complex halogenated aromatics is the fact that the halogen confers an appreciable amount of the fire retardancy property of the phosphazenes. For this reason, it is desirable that the amount of halogen, on a percentage basis, be rather high. In other words, all things considered, it is usually desirable not to 'dilute' the amount of halogen by having substituents which do not confer another useful property.

To achieve the desired balance of properties in the molecule, one may use a mixture of halogenated compounds to prepare the fire retardant phosphazene. For example, it is known that naphthalene compounds can be substituted with a comparatively high number of halogen atoms. Thus, it is suggested that one may use a halogenated naphthol together with a less complex material such as p-bromophenol to form a mixed phosphazene useful as a fire retardant for polyester.

Generally, because of their availability, I prefer that the halogenated hydroxy aromatic be a halogenated phenol. For purposes of this invention the term "halogenated phenol" shall mean a derivative of phenol, $C_6H_5OH$, in which one or more or the ring hydrogens is substituted with a halogen atom, preferably selected from chlorine and bromine. Of the halogenated phenols, I prefer the bromine compounds although the chlorine compounds are quite useful. Thus, to a great extent, the following description pertains to those aspects of the invention involving bromo compounds. However, it is to be understood that this is for purposes of brevity only, and the analogous chlorinated starting materials and phosphazenes derived from chlorinated hydroxy compounds, and polyesters containing same are also embodied within this invention. The bromophenols may be mono-, di-, or tribromophenols; the chlorine analogs are also useful.

Applicable brominated and chlorinated hydroxy compounds are illustrated by those described by Formulas (I) and (II) above. Of those compounds, the ones which have up to two alkyl radicals bonded to the benzene ring are preferred. Because of their more ready availability, those having no alkyl groups or one alkyl group are more preferred.

As indicated above, the exact size and configuration of the organic group bonded to the benzene ring is not critical, and more heavily substituted phenols, e.g. those with more than three organic groups as well as those with groups having more than three carbons can be used, if desired. Use of phenols with halogenated side chains such as where R is Formula (I) is —$CH_2Br$ or —$CH_2CH_2Br$ is part of this invention.

Of the applicable halogenated hydroxyaromatics, the following are representative:

(a) o-bromophenol
(b) p-bromophenol
(c) 2,6-dibromophenol
(d) 2-methyl-4-bromophenol
(e) 2-methyl-4,6-dibromophenol
(f) 2-ethyl-4-bromophenol
(g) 2-ethyl-4,6-dibromophenol
(h) 4-methyl-2-bromophenol
(i) 2,6-dimethyl-4-bromophenol
(j) 2-methyl-3,4,5,6-tetrabromophenol
(k) pentabromophenol
(l) 2,6-diethyl-p-bromophenol
(m) 2,4,6-trimethyl-3-bromophenol
(n) 2,4,6-tribromophenol
(o) 2,3,5,6-tetramethyl-4-bromophenol The phosphonitrilic halide starting materials for this invention can be phosphonitrilic chloride $(PNCl_2)_n$ or phosphonitrilic bromide $(PNBr_2)_n$ where $n$ is 3 or greater. Because of their more ready availability, the phosphonitrilic chlorides are preferred.

Phosphonitrilic chlorides used to prepare the phosphazene fire retardants can be produced by a) reacting $PCl_5$ with ammonium chloride; U.S. Pat. No. 3,367,750,
b) reacting $PCl_5$ with ammonia, U.S. Pat. No. 3,656,916,
c) reacting ammonia with phosphorus with chlorine; U.S. Pat. No. 3,658,487,
d) reacting phosphorus trichloride, chlorine and ammonium chloride; U.S. Pat. No. 3,359,080, and
e) reaction of ammonium chloride and $PCl_5$ in the presence of certain metal salts; U.S. Pat. Nos. 3,407,047, 3,462,247 and German Pat. No. 2,321,221.

Other known procedures for producing phosphonitrilic halides are found in Am. Chem. J. 19, 728 (1897), Berichte, 57B, 1343 (1924), U.S. Pat. No. 2,788,286; 3,008,799; 3,249,397; 3,347,643; 3,372,005; 3,378,353; 3,379,511 and Netherlands Pat. No. 70/05128.

The procedures of the aforementioned patents and publications are incorporated by reference herein as if fully set forth.

It is known that the molecular weight of linear $PNCl_2$ can be increased by heating under a blanket of nitrogen; James M. Maselli et al, *Phosphonitrilic Laminating Resins*, Technical Report AFML-65-314 June (1965), prepared by the Research Division of W. R. Grace and Company, Clarksville, Maryland under USAF Contract No. AF 33(615)–1640; AD 815233. Thus, as set forth on page 47 of that report, a sample of $PNCl_2$ with a molecular weight of 700 by vapor phase osmometry and prepared by the procedure described in Section II (Part A.1) of the report was placed in a resin kettle fitted with a nitrogen inlet stirrer and exhaust tube condenser. The resin kettle was heated to 250° ± 10° C. for a total of 55 hours while the polymeric ($PNCl_2$) was stirred under a blanket of dry nitrogen. Samples of the polymer were taken at selected intervals of time during the heating for molecular weight determination. The data given are as follows:

| Time (hours) | Molecular Weight (VPO) |
|---|---|
| Start | 700 |
| 10 | 1200 |
| 40 | 3200 |
| 55 | 6900 |

When heating was continued for an additional 8 hours at temperatures in excess of 250° C. the viscous, soluble oil (m. wt. 6900) was converted to the familiar insoluble "inorganic rubber". Such compositions can be used as starting materials for this invention.

It is also known that poly(dichlorophosphazene) can be prepared by polymerization of cyclic trimer to yield a product having molecular weights in the range of $1 \times 10^6$ to $2 \times 10^6$; confer Allcock, *Phosphorus-Nitrogen Compounds*, Academic Press, N.Y. (1972) pages 309–310, 346–352. These compositions can be used as starting materials for this invention.

Furthermore, it is known that cyclic phosphonitrilic chlorides are soluble in solvents such as ligroin while linears are not; Audrieth et al, Rev. 32, 111–127 (1943). The solvent-cyclic fraction can be separated from the linears and subjected to further treatment to separate out cyclic trimer. For example, the solution with the cyclics can be heated to 150–190° C. at about 60 mm. Hg while passing vaporized heptane through the solution. This procedure removes cyclic trimer. The residue from which the trimer is removed contains other cyclics, e.g. $(PNCl_2)_4$, $(PNCl_2)_5$, $(PNCl_2)_6$, $(PNCl_2)_7$ and may also contain higher cyclic oligomers. Such mixtures can be used to prepare halophosphazenes of this invention.

The phosphonitrilic halide starting material can be linear, cyclic, or mixtures of these. In general, processes for producing phosphonitrilic halides provide a crude mixture containing from 50 or less to about 95 weight percent cyclic materials and the remainder linears. Although pure cyclic and linear isomers can be separated and used as the starting materials of this invention, the cyclic and linear mixed isomers are satisfactory and preferred because of their cheaper, more practical processes of production. The mixed cyclic and linear isomers of phosphonitrilic halide are generally oily, viscous liquids, although the pure materials may be solid under normal ambient conditions.

In a preferred embodiment the products of this invention are made from compositions having 65–75 percent cyclic phosphonitrile chloride polymers and 35–25 percent linear materials. In these starting materials, the cyclic distribution ranges from 60–75 percent trimer, 18–24 percent tetramer, and 7–12 percent pentamer. Other preferred starting materials have cyclic contents ranging from 80–85 percent cyclic up to 95 or 100 percent cyclics.

Thus, in a more preferred embodiment, the phosphonitrilic chloride starting material is a mixture within the following composition range:

|  | Weight per cent |
| --- | --- |
| Cyclic trimer | 35–85 |
| Cyclic tetramer | 20–8 |
| Cyclic pentamer | 12–4 |
| Cyclic hexamer | 7–1 |
| Cyclic heptamer | 6–0 |
| Linears and higher cyclics | 20–2 |

To prepare phosphazenes, the phosphonitrilic halides described above may be reacted with metal derivatives of the phenols. Of the metals, the alkali metals are preferred. Sodium and potassium are highly preferred because of their availability, and sodium is more preferred because of its reactivity and relative inexpensiveness. The metal derivative is prepared by reacting the metal with the phenol in any convenient manner. For example, sodium can be reacted with a p-bromophenol using an inert hydrocarbon such as benzene or p-dioxane as a reaction mixture. The sodium may be in the solid state or may preferably be melted by heating to about 110° C. When using molten sodium, it is convenient to employ a reaction medium which has a boiling point above the solidification temperature of the sodium. Toluene, kerosene, or No. 9 oil can be employed. Kerosene or No. 9 oil may be somewhat difficult to remove from the product, and accordingly, toluene is a reaction medium of choice.

It is convenient to use an excess of the phenol as a precaution against unreacted sodium. Good results are obtained utilizing a 10–20 weight percent excess. However, greather or lesser excesses can be used.

The alkali metal derivative of the brominated phenol is reacted with the phosphonitrilic halide. This can be accomplished by admixing the phosphonitrilic halide with the mixture of alkali metal derivative, solvent and excess phenol prepared as described above. Typical solvents which can be employed are p-dioxane and tetrahydrofuran.

It is preferred that the alkali metal derivative be in substantial excess over the theoretical requirement. By a substantial excess is meant an excess of at least about 5 weight percent. It is convenient to use amounts of phenoxide which are from about 5 to about 15 weight percent excess over the theoretical requirement.

In many instances, the reaction is rapid and exothermic at the beginning and requires no heating. After mixture of the reactants is complete, it may be convenient to heat the resultant reaction mass and hold it at reflux temperature for such time as analysis indicates complete reaction. Reaction times in the range of from 12 to 10 hours can be used. This is somewhat dependent upon the reaction temperature which is usually within the range of from ambient to 110° C.; more preferably from about 55° to about 110° C.

After conduction of the reaction, the excess free hydroxy compound and the solvent are removed by distillation or other suitable means. These can be recycled for later use.

As with the preparation of the metal derivative of the hydroxy compound, the phosphazene synthesis proceeds well at ambient pressure. Accordingly, atmospheric pressure is of choice. However, greater or lesser pressures can be used if desired.

When preparing mixed phosphazenes, the phosphonitrilic halide is reacted with a mixture of metal derivatives of two or more phenols. Thus, for example, one can prepare mixed phosphonitrilic halide condensation products by reacting the sodium derivative of a mixture of 2-bromophenol and 2,6-dibromophenol.

One can prepare the phosphonitrilic halide condensation products by reacting the brominated phenol with the phosphonitrilic halide in the presence of a tertiary amine such as pyridine. In this regard, one may use the method set forth in Netherlands Pat. No. 71/06772.

This affords a milder technique which can be used in those instances where there may be appreciable attack of a bromine substituent by alkali metal.

Alternatively, one can prepare the metal bromophenoxy derivative by reacting the bromophenol with the corresponding metal hydroxide. Reaction conditions similar to those described above for use with the alkali metal can be used. As referred to above, the halogenated, hydroxy aromatic phosphazenes useful as fire retardants have the structural backbone

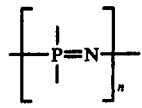

with the hydroxy aromatic radicals bonded to phosphorus through two of the valences shown. The molecular weight can be from where $n$ equals 3 or higher. When $n$ equals 10 or more the formula represents new compounds of this invention. The formula represents pure compounds as well as mixtures obtained from mixed phosphazene starting materials. As explained above, mixed phosphazene starting materials are preferred, hence, the halogenated hydroxy aromatic fire retardants represented by the formula frequently are mixtures.

For phosphazenes having a molecular weight of up to 20,000 the number average molecular weight can be determined by vapor phase osmometry. For these materials of molecular weight of from about 10,000–1,000,000, the number average molecular weight can be determined by membrane osmometry. For materials of molecular weight of up to 5,000,000 weight average molecular weight can be determined by light scattering photometry.

It is to be understood that the halogenated hydroxy aromatic phosphazene fire retardants may contain a minor amount of residual halogen resulting from incomplete substitution of the halogen atoms in the phosphonitrilic halide with hydroxy aromatic compound. It is preferred that the amount of residual halogen be at a level as low as convenient; preferably the amount of residual halogen is less than 2 weight percent, or more preferably less than 1.0 weight percent.

EXAMPLE 1

A polyester resin, Polylite 31-007 from Reichhold Chemicals, Inc. 57 parts, was blended with 43 percent styrene and the amount of additive shown below. The mixture was cured at 50° C. overnight using 1 percent benzoyl peroxide. Thereafter, it was post-cured at 80° C. for 3 hours. Flame resistance was demonstrated by the Limiting Oxygen Index Standard Test, LOI.

| | Concentration Weight percent | LOI | Remarks |
|---|---|---|---|
| Hexa-p-bromophenoxy phosphazene* | 15 | 21.6 | Very slow melt |
| Blank | — | 18.4 | Very slow melt |

*(p-Bromophenyl) derivative of a preparation of phosphonitrilic dichloride which is a 98 percent mixture of trimer and tetramer available from Research Organic-Inorganic Chemical Corp. 11686 Sheldon St., Sun Valley, California 91352. Polylite 31-007 referred to above is a rigid low viscosity general purpose polyester resin of low reactivity. It is a basic resin for the preparation of molding, casting, and coating formulations. The properties of liquid 31-007 Polylite are as follows:

| | |
|---|---|
| Viscosity, Brookfield, cps at 77° F. | 275–400 |
| Color, APHA, Max | 100 |
| Specific Gravity | 1.10–1.12 |
| Weight per Gallon, lbs | 9.3–9.5 |
| SPI Gel Test | |
| Gel Time, Mins | 4'30"–6'30" |
| Gel to Peak, Mins | 3'00"–4'-00" |
| Peak Exotherm Temp. ° F. | 375–395 |

Similar results are obtained when the bromophenoxy derivative is made from metabromophenol and brominated phenols (a)-(m) above and PNCl$_2$ preparations having any of the compositions in Tables 1-5 of Emsley, supra, (or analogous PNBr$_2$ compositions) when mixed with the polyester in amounts from 2 to 40 weight percent.

EXAMPLE 2

Sodium metal (21.3g, 0.93 m) was added (under N$_2$) to dry dioxane (200 g) and the mixture brought to reflux. Then, p-bromophonyl (181 g, 1.05m) in dry dioxane (150 g) was added at 99–104° over 30 minutes. After 90 minutes reflux, H$_2$ gas evolution had substantially ceased. The mixture was cooled to room temperature and a solution of 77 per cent cyclic phosphonitrilic chloride (36.0 g) in dry dioxane (168 g) was added over 5 minutes with a 25° exotherm. The mixture was then refluxed for a total of 7 hours 40 minutes and dioxane removed by distillation to form a semi-solid residue. The residue was shaken with benzene and the slurry transferred to a 4 liter separating funnel using a rinse of sodium hydroxide (30 g) in water (1 liter). The mixture was shaken and the lower layer was separated. The organic layer was washed with water (2 × 1 liter), using a few grams of NaCl in the last water wash to reduce an emulsive tendency in the lower layer. The organic layer was dried with MgSO$_4$, filtered through Celite and stripped at up to 70°/4 mm to give 118.5 g of product. Extraction of the rag layer gave 1.5 g of additional material. The total yield of hexa(p-bromophenoxy)phosphazene (120.0 g) was 99.3 per cent of theory. Elemental analysis:

| | Found | Calculated |
|---|---|---|
| C | 38.8 | 37.1 |
| H | 2.59 | 2.07 |
| Br | 37.2 | 41.2 |
| Cl | 0.0 | 0.0 |
| P | 8.05 | 7.97 |

EXAMPLE 3

For this preparation, 2,4-dibromophenol (93.0 g, 0.369 m) was dissolved in a solution of sodium hydroxide (13.6 g, 0.34 m) in water (100 ml). Toluene (600 ml) was added and the water removed by distillation into a Dean-Stark separator. Then, a 100 ml portion of toluene was removed by distillation and the resultant mixture cooled to 52° C. A solution of PNCl$_2$ (17.4 g, 0.15 m) in toluene (75 ml) was added to the slurry over 9 minutes. After 30 minutes at reflux, no reaction had appeared to take place, so toluene (350 ml) was distilled overhead and replaced by dry p-dioxane (350 ml). The dioxane addition caused an immediate solution of most of the slurry and the development of a powder blue color. Within a few minutes, solid particles re-formed and the mixture turned blue-gray and then gray. At reflux, and about 35 minutes after the p-dioxane addition, no further changes in the mixture's appearance was apparent. After 5 hours and 30 minutes reflux, the mixture was vacuum distilled to give a whitish solid. After shaking with 5 percent sodium hydroxide (300 ml) a coarse, sand-like solid remained. The product was treated with several organic solvents including benzene and ether. The mixture was vacuum filtered. The solid reside was water washed and oven dried to give 63.0 g of product. The organic layer of the filtrate was separated, dried over MgSO$_4$, filtered and stripped to give 19.0 g of a thick oil which quickly crystallized. The infrared spectra of the two isolated solids were virtually identical, and both melt above 180° in a wide range. The combined yield of hexa(dibromophenoxy) phosphazene reaction product is 82.0 g or almost 100 percent of theory. Elemental analysis:

|   | Solid Residue | Crystallized Oil | Calc'd |
|---|---|---|---|
| C | 26.4 | 27.6 | 26.4 |
| H | 1.34 | 1.47 | 1.11 |
| P | 5.59 | 5.66 | 5.67 |
| Br | 56.4 | 56.0 | 58.4 |
| Cl | 0.91 | 0.77 | 0.0 |

The phosphonitrilic chloride employed in Example 3 was the same type as employed in Example 1.

EXAMPLE 4

To show utility in linear polyester of phthalic acid and ethylene glycol, chips of this polymer were ground into small (0.080 mesh) particles. The particles were dried in a vacuum oven at 100° C. for 48 hours. After drying, the polyester was removed from the oven, cooled in a dessicator and sealed in jars to keep it free of moisture. Twenty two grams of this powdered polyester was combined with 2.5 g (10 percent) of flame retardant, mixed by hand and spread uniformly on mirror-finished aluminum foil within the frames of a Chase-type stainless steel mold 7 × 8 inches × 20 mil thick. This powdered polyester was covered with a uniformly stretched fiber glass gauze (100 den.) and covered with aluminum foil. The whole assembly was reinforced with steel plates and placed into a heated press at 280° C., 600 psi for 2 min. warmup and 2 min. mold. After 4 min. the assembly was removed from the press and allowed to cool for 10 min. The resultant sheet was conditioned at 73° F. and 50 percent relative humidity for 48 hours, cut into 2 × 6 inch sections and tested for Oxygen Index.

When this procedure was used to incorporate 10 weight percent of the hexa(bromo) derivatives of Example 2 and the hexa(dibromo) product of Example 3, the results were

|   | Limiting Oxygen Index |
|---|---|
| Blank | 20.5 |
| Product of Ex. 2 | 25.5 |
| Product of Ex. 3 | 25.9 |

Similar results are obtained when the bromophenoxy derivative is made from m-bromophenol, and brominated phenols (a)-(m) above and phosphonitrilic chloride preparations of Emsley, supra, (or analogous $(PNBr_2)_x$ compositions when admixed in the polyester at from 2 to 40 weight percent.

EXAMPLE 5

A 170 g sample of trimeric phosphonitrilic chloride was thermally polymerized at 250° C. in a sealed glass tube over a period of 48 hours. The high molecular weight, linear $PNCl_2$ polymer was separated from cyclic oligomers by dissolving the polymerization product in dry toluene (1200 ml) and precipitating the high polymer by adding an excess of dry n-heptane (2640 ml). The precipitated polymer (37.5 g, 22 percent conversion) was washed with heptane and dried under high vacuum at room temperature. The polymer was then dissolved in 915 ml of dry tetrahydrofuran (distilled from $LiAlH_4$).

A 174.1 g (1.01 mole) sample of p-bromophenol (99 percent purity) dissolved in 90 ml of dry tetrahydrofuran (THF) was added to a suspension of 22.6 g (0.983 mole) of sodium in 500 ml of refluxing THF. After the sodium had completely reacted (∼6 hours), the viscous polydichlorophosphazene-THF solution (37.5 g, 0.323 mole $PNCl_2$) was added over a period of 2 hours at a pot temperature of 64° C. The mixture was held at 64° C. for a total of 15 hours after the addition was complete. The viscous, white reaction mixture was then transferred to a dropping funnel and the poly(p-bromophenoxy)phosphazene was precipitated by pouring into 10 l. of distilled water. The precipitated product was a thin white fiber. The fiber (112 g, 88 percent yield) was dried under vacuum and then redissolved in 1800 ml of THF. The product was precipitated by addition into 10 l. of 5 percent NaOH, washed with distilled water (15 × 400 ml) and dried under vacuum. The resulting 99 g of poly(p-bromophenoxy)phosphazene was again dissolved in THF (1725 g). The product was precipitated by pouring into 5 l of methanol. The dried white resultant fiber weighed 94.3 g (75.0 percent yield). Product analyses: Cl, 0.7 percent; P, 7.93 percent (7.96 percent theory): bromophenol 33 ppm.

By the procedure exemplified above, high polymeric poly(dichlorophosphazene) is prepared, and this can be used to prepare products having a weight average molecular weight within the range of about $2 \times 10^5$ to about $2 \times 10^6$ and up to $2 \times 10^7$. Similar results are obtained when the p-bromophenol utilized above is replaced with o-bromophenol, and the other bromophenols designated (c) through (o) in the list above. Similar results are obtained when the bromo compounds are replaced with their chloro analogs.

Trimeric phosphonitrilic chloride suitable for the thermal polymerization can be made by the procedure set forth on pages 309–310 of Allcock, *Phosphorus-Nitrogen Compounds*, Academic Press, New York (1971).

EXAMPLE 6

A solution of 226.7 g (1.31 moles) of p-bromophenol (99 percent purity) in 210 g of tetrahydrofuran (THF) was added dropwise over a period of 15 minutes to a suspension of 30.0 g (1.30 mole) of sodium in 402 g of refluxing THF. The mixture was heated at reflux (67° C) for 6 hours to complete the formation of the sodium p-bromophenoxide. A 50.1 g (0.43 mole $PNCl_2$) sample of oligomeric, heptane-soluble $PNCl_2$ from which most of the trimer was removed by distillation (VPC analysis 1.5 percent trimer, 28.8 percent tetramer, 25.3 percent pentamer, 13.0 percent hexamer, 8.5 percent heptamer) was dissolved in 50 g of THF. The $PNCl_2$ solution was added to the sodium p-bromophenoxide slurry over a period of 45 minutes with an increase in the pot temperature of from 50° C. to 65° C. The mixture was held at reflux for a total of 15 hours. The reaction mixture was then stripped of solvent using a rotary evaporator, and 500 ml of benzene was added to the solid. The benzene solution was washed with 10 percent NaOH (250 ml), water (250 ml), 1 M HCl (250 mole) and then with water (3 × 200 ml). The organic phase was dried over anhydrous $Na_2SO_4$ and then filtered. The yellow solution was treated with 3.0 g of activated carbon (Nuchar, C-115-N) and filtered through a bed of Celite. The light yellow solution was stripped of solvent using a rotary evaporator to give 134.5 g (80 percent yield) of a light yellow oil. The product contained bromophenol impurity, so a 90 g sample of the oil was dissolved in 450 ml of toluene and washed with 10 percent NaOH (3 × 150 ml) and water (4 × 250 mole). The toluene solution was then dried over anhydrous MgSO$_4$, filtered and stripped of solvent to give 86.9 g of light yellow oil. Product analysis: Cl, 0.11 percent; P, 8.16 percent (7.96 percent theory); Br, 38.9 percent (41.2 percent theory), bromophenol, 390 ppm; mole weight in benzene, 2130.

The oligomeric heptane soluble phosphonitrilic chloride was essentially cyclic since it is known that ordinary linear materials are not very soluble in heptane. By use of the term "essentially cyclic" in this invention, compositions are designated in which linear phosphonitrilic chlorides have been removed by extraction with n-heptane, ligroin or other equivalent solvent. In general, the essentially cyclic PNCl$_2$ compositions have less than about 5 weight percent linear materials. "Essentially trimer free" means < 5 weight percent trimer.

The VPC analysis given above is not complete as to the entire composition of the starting material, since the method employed differentiates (PNCl$_2$)$_3$, (PNCl$_2$)$_4$, (PNCl$_2$)$_5$, (PNCL$_2$)$_6$ and (PNCl$_2$)$_7$ but does not differentiate the higher cyclics. Analogous materials of up to (PNCl$_2$)$_{17}$ have been reported.

The molecular weight of pure [(C$_6$H$_4$OBr)$_2$PN]$_4$ is 1556. For the p-bromophenol analog prepared from cyclic (PNCl$_2$)$_{17}$ the molecular weight is 6613. The molecular weight of products prepared by the procedure of this example from the bromophenols disignated (c) to (o) above and their chloro analogs would be analogous and according to the molecular weight conferred by the particular halogenated aromatic hydroxy compound employed.

In a similar manner, phosphazenes can be prepared by reacting p-bromophenol with essentially linear phosphonitrilic chloride preparations having a molecular weight of 1200, 3200 and 6900 prepared by the method disclosed in AD 815233, supra.

Likewise related materials can be made using the technique of the above example to react the brominated compounds designated (a) and (c) to (o) above with the phosphonitrilic chlorides mentioned above prepared by the procedure of AD 815233, supra. Similarly, utilizing this procedure other hydroxy aromatics designated by formulas (I) or (II) above such as the chloro analogs of compounds (a)-(o) and 2,4-dibromophenol can be used.

The procedure can be used to prepare essentially linear phosphazenes of from 10,000 to 34,000 molecular weight.

Following Examples 1-3 and 5-6, phosphazenes can be prepared from mixtures of p-bromophenol and 2,4-dibromophenol. The preferred mixtures have at least 90 weight percent p-bromophenol although greater and lesser amounts can be used. More preferably, there is about 2-5 weight percent dibromophenol in the mixture.

The products of Examples 1-3 and 5-6 are incorporated in poly(ethyleneterephthalate) and poly(1,4-cyclohexylmethyleneterephthalate) so that the flame retardant concentration is from 2 to 40 weight percent. The treated polyester can be utilized to prepare flame retardant polyester fabric. The fire retardant polyester fiber can be blended with cotton or wool. For example, a blend of 65/35 (polyester/cotton), 50/50 (polyester/cotton) and 80/20 (polyester/wool can be used. Such fabrics can be used to prepare clothing. Likewise, the mixture of equal parts polyester and cotton can be employed to prepare sheets and pillow cases. Preferably, the molecular weight of phosphazene in the polyester is from about 3900 to about 2 × 10$^7$.

Also, the fire retardants of this invention may be applied to the surface of the polyester to be treated. This can be done by contacting the fire retardant, or a solution, emulsion, dispersion, or suspension thereof, with the substrate by spraying, dipping, spreading, rolling or similar technique such as use of a textile pad bath. If a solution or suspension or similar mixture of fire retardant and solvent is used, the product is further treated with heat to evaporate the solvent or solvents employed. Prior to this the treated material can be treated to remove excess liquid by squeezing, centrifuging, pressing, or other operations.

Treatment of the surface can efficaciously be conducted, for example, using a polyester film, fiber, thread, cloth, or garment. In general, it is desirable to deposit enough fire retardant so that the percentage concentration thereof is 2-40 weight percent, preferably 2-30 percent and more, preferably 10-20 percent.

The results of the above examples suggest that condensation products of phosphonitrilic dihalide (chloride or bromide) and brominated phenol can be used to flame retard other materials such as polystyrene, polyvinyl chloride, polyurethane, polycarbonate, polyamide, and epoxy resins.

For polystyrene, molding powders or expandable beads can be prepared. In addition, the surface of an expandable bead can be impregnated with mixtures of the fire retardant additive and organic media such as propanol, methanol, toluene, etc. and then dried.

As to polymers suggested, reference is made to Floyd, *Polyamide Resins* (1958); and Christopher and Fox, *Polycarbonates*, all published by Reinhold Publishing Corp., New York, N.Y. Polymer compositions disclosed therein are incorporated by reference herein as if fully set forth. To illustrate this portion of the invention the following compositions which may be treated with from 2 to 40 weight percent of a bromophenoxyphosphazene prepared from any of the PNCl$_2$ compositions set forth in Tables 1-5 of Emsley, supra.

| | |
|---|---|
| Polystyrene molding powder | |
| Styrene | 10,000 parts (by weight) |
| Barium sulfate | 100 parts |
| Benzoyl peroxide | 25 parts |
| Water | 20,000 parts |
| Polystyrene expandable bead | |
| Styrene | 20,000 parts |
| Sodium pyrophosphate | 2 parts |
| Hexane | 1,500 parts |
| Benzoyl peroxide | 70 parts |
| Water | 20,000 parts |
| Protective colloid | 70 parts |
| PVC composition | |
| Polyvinyl chloride | 100 parts |
| Dioctyl phthalate | 40-50 parts |
| Tin stabilizer | 9 parts |

In addition, epoxy resins, polyamides, and polycarbonates disclosed in the above-cited books can be treated with 2 to 40 weight percent of a phosphazene additive of this invention.

I claim:

1. As a composition of matter, polyester stabilized with a fire retardant amount of a phosphazene that is a reaction product of a phosphonitrilic halide and a chlorinated or brominated monohydroxyaromatic compound, said polyester being selected from unsaturated polyester resin and fiber-forming polyester.

2. A composition of claim 1 comprising (a) a fiber-forming polyester condensation product of a diol and a dicarboxylic acid, or ester of a dicarboxylic acid, selected from the class consisting of isophthalic acid, terephthalic acid and saturated aliphatic dibasic acids of 2 to about 10 carbon atoms, and (b) a fire retardant amount of a phosphazene that is a reaction product of a phosphonitrilic halide and a chlorinated or brominated monohydroxyaromatic compound.

3. A composition of claim 1 wherein said compound has an isolated benezene nucleus of up to about 10 carbon atoms.

4. A composition of claim 3 wherein said monohydroxyaromatic compound with an isolated benzene nucleus is a chlorinated or brominated phenol.

5. A composition of claim 4 wherein said phenol is selected from the class consisting of p-bromophenol, 2,4-dibromophenol, and mixtures thereof.

6. A composition of matter comprising (a) a fiber-forming polyester of a diol and a dicarboxylic acid selected from the class consisting of isophthalic acid, terephthalic acid and saturated aliphatic dibasic acids of 2 to about 10 carbon atoms, and (b) a fire retardant amount of a phosphazene having the formula

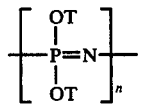

where $n$ is 3 or more and T is a monohydroxy aromatic radical having the formula

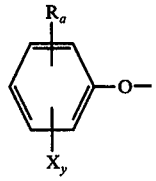

wherein R is an alkyl group of up to about 3 carbon atoms, $a$ is an integer of value 0-4 such that the number of carbon atoms in said aromatic compound does not exceed about 10, X is selected from chlorine and bromine, and $y$ is an integer of value 1-5.

7. A composition of claim 6 wherein said phosphazene has a melting point above about 200° C.

8. A composition of claim 6 wherein said phosphazene is essentially cyclic and essentially free of trimer, and at least 50 weight percent thereof is composed of cyclic tetramer, cyclic pentamer, or mixture thereof, the molecular weight of said phosphazene being from about 1900 to about 6600.

9. A composition of claim 6 wherein said phosphazene is essentially linear and the molecular weight is from about 4000 to about 6000.

10. Polyester stabilized with a flame retardant amount of condensation product of phosphonitrilic dihalide and p-bromophenol, said polyester being selected from the class consisting of saturated polyester fiber made from ethylene glycol and an acid selected from the class consisting of isophthalic and terephthalic acid, an unsaturated polyester resin made from said alcohol and a mixture of maleic acid and another acid selected from the class consisting of isophthalic and terephthalic acid, said mixture being crosslinked with a material selected from the class consisting of divinylbenzene and styrene.

11. A polyester composition of claim 10 wherein the concentration of said condensation product is from about 5 to about 30 weight percent.

12. A polyester composition of claim 10 wherein said condensation product is a p-bromophenyl derivative of a phosphonitrilic chloride.

13. An unsaturated polyester resin composition of claim 10.

14. A saturated polyester fiber composition of claim 10.

15. Polyester stabilized with a flame retardant amount of condensation product of phosphonitrilic dihalide and a brominated phenol having the formula

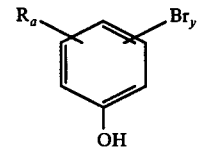

wherein R is an alkyl radical of up to about 3 carbon atoms, $a$ is an integer of value 0-3 such that the total number of carbon atoms in radicals appended to the ring is not more than about 4 and $y$ is an integer of value 1-5; said polyester being selected from the class consisting of saturated polyester fiber made from ethylene glycol and an acid selected from the class consisting of isophthalic and terephthalic acid, and unsaturated polyester resin made from said alcohol and a mixture of maleic acid and another acid selected from the class consisting of isophthalic and terephthalic acid, said mixture being crosslinked with a material selected from the class consisting of divinylbenzene and styrene.

16. A polyester composition of claim 15 wherein the concentration of said condensation product is from about 5 to about 30 weight percent.

17. A polyester composition of claim 1 wherein said condensation product is a 2,4-dibromophenyl derivative of phosphonitrilic dichloride.

18. An unsaturated polyester resin composition of claim 15.

19. A saturated polyester fiber composition of claim 15.

* * * * *